United States Patent [19]

Pao

[11] Patent Number: 4,693,245
[45] Date of Patent: Sep. 15, 1987

[54] NUCLEUS SPLITTER

[76] Inventor: David S. C. Pao, 95 High Point Dr., Churchville, Pa. 18966

[21] Appl. No.: 782,490

[22] Filed: Oct. 1, 1985

[51] Int. Cl.[4] ............................................. A61F 17/32
[52] U.S. Cl. ..................................... 128/305; 128/346
[58] Field of Search ........................ 128/305, 346, 320; 604/22

[56] References Cited

U.S. PATENT DOCUMENTS

| | | | |
|---|---|---|---|
| 1,601,035 | 9/1926 | Nauth | 128/346 |
| 1,677,209 | 7/1928 | Rose | 128/305 |
| 3,750,671 | 8/1973 | Hedrick | 128/305 |
| 3,825,011 | 7/1974 | Frewer | 128/346 |
| 3,937,222 | 2/1976 | Banko | 128/305 |
| 4,058,126 | 11/1977 | Leveen | 128/305 |
| 4,106,508 | 8/1978 | Berlin | 128/346 |
| 4,368,734 | 1/1983 | Banko | 128/305 |
| 4,499,898 | 2/1985 | Knepshield et al. | 128/305 |
| 4,538,611 | 9/1985 | Kelman et al. | |
| 4,552,146 | 11/1985 | Jensen et al. | 128/305 |
| 4,641,651 | 2/1987 | Card | 128/305 |

Primary Examiner—Richard J. Apley
Assistant Examiner—H. Macey
Attorney, Agent, or Firm—Woodcock Washburn Kurtz Mackiewicz & Norris

[57] ABSTRACT

A device for fragmentation of the nucleus of an eye lens, in vivo, including a working tip adapted to be passed through a limbal incision in the eye and beneath the nucleus of the lens, in vivo, and includes a hollow tubular portion for guiding an elongated member, a platform portion extending from the hollow tubular portion and one or more points or tines at the extreme end of the platform portion all adapted for immobilizing the nucleus while the elongated member is advanced into and removed from the nucleus, guided by the hollow tubular portion, causing its fragmentation. A modified syringe embodiment is described in which the elongated splitting member is coupled with and manipulated by means of a syringe plunger.

6 Claims, 8 Drawing Figures

NUCLEUS SPLITTER

FIELD OF THE INVENTION

In cataract removal and certain other ophthalmic surgical procedures, it is necessary to remove the nucleus of the lens. This is typically accomplished by making a small, limbal incision and fragmenting the nucleus in vivo into pieces sufficiently small to pass through the incision. Nuclei vary in hardness some being soft and easily fragmented into smaller pieces with a blunt-tipped or sharpened instrument pressed repeatedly against the nucleus surface. Harder nuclei, though they are not as hard as any instrument the surgeon may use, present some difficulties. The reduction of nuclei to small fragments through a limbal incision is tedious and time consuming. Moreover, because of the angle at which the tool must be used, it is sometimes difficult for the surgeon to bring pressure to bear against the nucleus surface and there is the danger of damaging surrounding tissue if the instrument were to slip. There is also the danger, during the procedure that the surgeon may penetrate completely through the nucleus damaging the underlying tissue.

SUMMARY OF THE INVENTION

It is a first object to provide a method and device for fragmenting nuclei, including "hard" nuclei, in vivo.

It is yet another object of the invention to provide a method and device for safely fragmenting nuclei in vivo.

It is yet another object to provide a device for fragmenting nuclei, in vivo, which can be manipulated with one hand if desired.

It is another object to provide a device which can simultaneously be used to fragment nuclei, in vivo, and introduce irrigation so as to clear the working field and more quickly remove nucleus fragments.

According to the invention there is provided a device which first is adapted to engage and immobilize the nucleus, in vivo and second to allow force to be applied against the engaged and immobilized nucleus so as to fragment it.

A preferred embodiment device is described for performing the aforesaid procedure. The device is based upon a modified syringe and needle but other equivalent mechanical structures can be used. A modified hollow needle has, at its distal tip, a projecting elongated platform which is adapted to be passed through a limbal incision and beneath the nucleus, in vivo. Projecting outwardly and transversely from the platform are one or more points or tines adapted for piercing and holding the nucleus. Coupled with the syringe plunger is a moveable, elongated splitting member with a tip adapted for applying force against and penetrating the nucleus in vivo. The elongated member passes through and is guided by a hollow, tubular, intermediate portion of the modified needle which constrains the movement of the elongated member along a center line of that portion through the captured nucleus. The elongated member is moved towards and away from the projecting tines, into and from the nucleus, by simple movement of the coupled syringe plunger back and forth within the syringe body. In addition to being used to pierce and hold the nucleus, the tines can be positioned "behind" the nucleus opposite the portion of the nucleus surface contacted by the splitting member to immobilize the nucleus.

Other advantages will be apparent to those skilled in the art upon examination of the accompanying drawings and following detailed description of the invention.

DETAILED DESCRIPTION OF THE INVENTION

Figure 1:
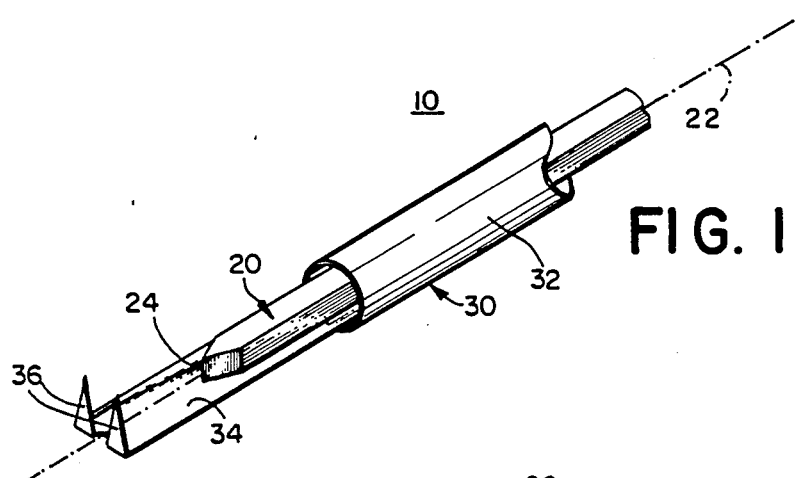
FIG. 1 is a diagrammatic perspective view of the working tip of a nucleus splitting subassembly of the invention.

FIG. 1 depicts a simple, nucleus splitting subassembly 10 of the invention which is formed by a nucleus penetrating member 20 slidably movable through the hollow interior of a guiding and nucleus securing element 30. The guiding and securing element 30 includes a hollow, tubular portion 32 which centers and restrains the movement of the nucleus penetrating member 20 along a central axis 22 of the member. The guiding and nucleus securing element 30 also includes at one end thereof, a platform portion 34 extending from an end of the hollow tubular portion 32 and, at the extreme distal end of the platform surface 34 a pair of tines 36 turned up at an approximately right angle to the plane of the platform portion 34. At its end proximal to the tines 36, the nucleus penetrating member is provided with a nucleus cutting edge 24. The tines 36 immobilize the nucleus as the cutting edge 24 is brought to bear against it. The nucleus may be positioned between the tines 36 and the cutting edge 24 or, preferably, impaled on the tines 36 for splitting. Note that the element 30 is sufficiently narrow and thin so that the tines 36, platform portion 34 and at least a portion of the hollow tubular portion 32 can be inserted through a small limbal incision into the anterior portion of the eye.

Figure 2:
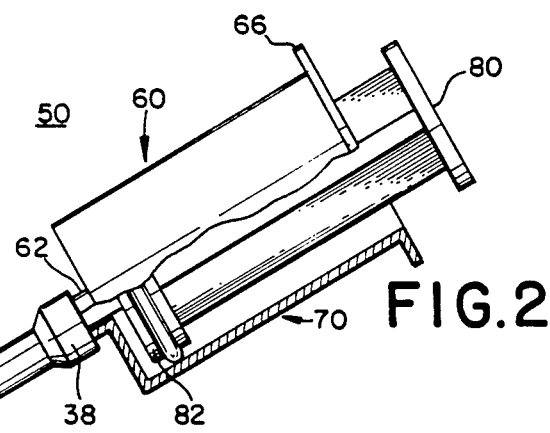
FIG. 2 is a diagrammatic, partially sectioned, side elevation of a nucleus splitting device incorporating the nucleus splitting subassembly of FIG. 1.

There is depicted in FIG. 2 a nucleus splitting apparatus 50 incorporating the nucleus splitting subassembly 10 coupled with a modified syringe 60 which is used to manipulate the assembly 10 in advance and withdraw the cutting edge 24 with respect to the tines 36. The guiding and nucleus securing element 30 includes at an extreme end opposite the tines 36 a female syringe coupling portion 38 adapted for coupling the element 30 with the male connector 62 of a standard syringe body 70. The modified syringe 60 includes the standard syringe body 70 housing a plunger 80 slidably movable through the hollow interior of the syringe body 70 along its center line. A circumferential flange 66 is provided at the end of the syringe body 70 opposite the male connector end 62. The syringe 60 is modified in that the end of the nucleus penetrating member 20 opposite the cutting edge 24 is coupled to the head 82 of the plunger 80 so that movement of the plunger 80 towards and away from the male connector end 62 of the syringe body 70 moves the cutting edge 24 of the member 20 towards and away from the tines 36.

The guiding and nucleus securing element 30 can be formed by modifying a conventional syringe needle. The extreme distal tip of the needle is ground down until only a portion of its original tubular structure remains which forms the platform portion 34. The extreme distal tip is then notched to form two distal tips which, when turned approximately 90 degrees, form the tines 36.

Based upon my own measurements, I have found the average eye nucleus to be about 7 mm in maximum diameter and about 3 mm in maximum thickness transverse to the maximum diameter. I therefore suggest that the length of the platform portion 34 be about 8 mm or more in length so that the full length of an average nucleus can be accommodated between the tines 36 and the extreme distal end of the tubular portion 32 of the element 30. I further found that tines about 0.3 mm in height are sufficient to engage and affix the nucleus.

Figure 3:
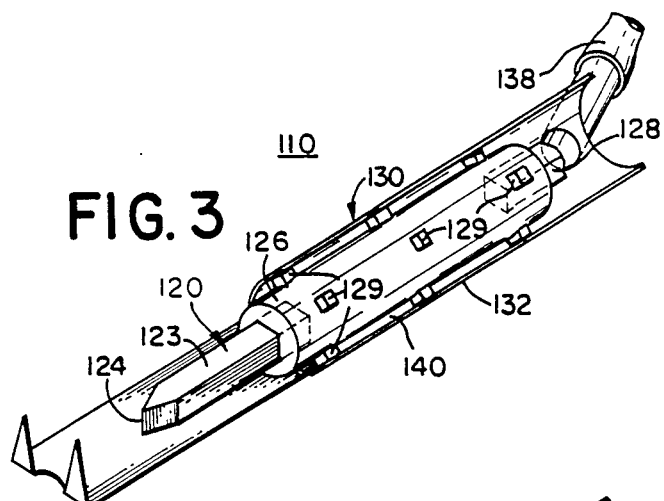
FIG. 3 is a diagrammatic, partially sectioned, perspective view of another nucleus splitting subassembly embodiment of the invention preferred where the introduction of irrigation into the eye is desired.

Referring now to FIG. 3, there is depicted diagrammatically a nucleus fragmenting subassembly 110, only the distal end of which is depicted, which is preferred when it is desired to introduce irrigation into the eye chambers during a nucleus splitting procedure. The guiding and nucleus securing element 130 is like the element 30 but is additionally provided with a hollow, fluid infusion coupling 138 projecting from a side wall of the hollow tubular guiding portion 132 of the element 130 for introducing fluid into the portion 132. A composite nucleus penetrating member 120 is depicted and includes a cutting head 123 with cutting forward edge 124, a central coupling section 126 and a connected elongated member 128 extending from the section 126 and coupled with the head of a syringe plunger or similar element for movement within the hollow tubular portion 132. Circumferentially arrayed on the outer, circumferential surface of the coupling section 128 are a plurality of radially extending pylons or the like projections 129 which serve to center the coupling section 126 and member 120 within the tubular portion 132 and provide and maintain a gap 140 between the outer side wall of the coupling section 126 and the interior wall of the hollow tubular section 132.

Figure 4:
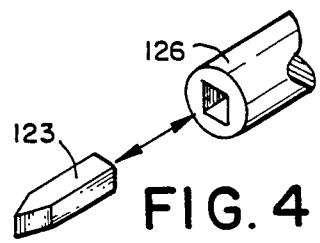
FIG. 4 depicts diagrammatically yet another embodiment nucleus splitting subassembly of the invention.

As is further depicted in FIG. 4 it is envisioned that the head 123 be made removably insertable into the working end of the coupling section 126 for replacement after use.

Figure 5:
FIG. 5 depicts diagrammatically a nucleus splitting subassembly of the invention incorporating a replaceable splitting blade.

Referring now to FIG. 5 yet another envisioned embodiment nucleus splitting assembly 210 in which the guiding and nucleus securing element 230 is provided with a curved platform portion 234 which drops away from and is concave with respect to the center line 22 of the penetrating member 20. In this embodiment the tines 236 are no longer approximately perpendicular to the center line 22 of the member 20 but remain generally transverse to the members, angled back towards the tubular portion 232 of the element 230. It is believed that this configuration may make insertion of the tines 236 and platform portion 234 of the subassembly 210 beneath a nucleus, in vivo, easier.

Figure 6:
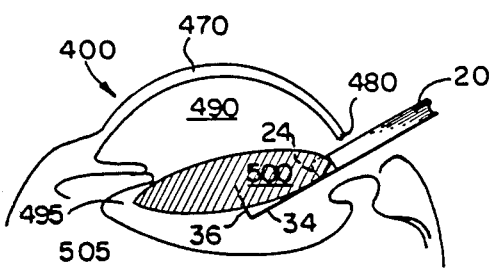
FIG. 6 depicts diagrammatically the positioning of the device to engage a nucleus.
Figure 7:
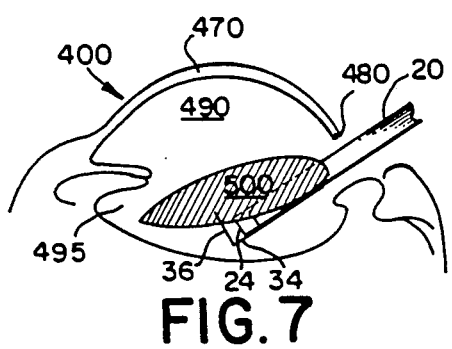
FIG. 7 depicts the diagrammatically the operation of the device to split the nucleus.
Figure 8:
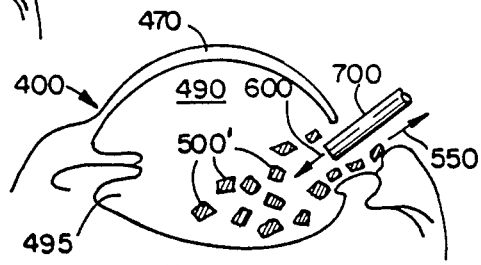
FIG. 8 depicts diagrammatically the expression of nucleus fragments after splitting.

The envisioned use of the instrument is depicted diagrammatically in FIGS. 6-8. The procedure for an extra-capsular nucleus extraction involves a limbal incision 480 through the corneosclera layer 470 of the eye 400. After the removal of the cortical material from the anterior chamber 490, the extreme, tined end of the nucleus splitting subassembly 10 is passed through the incision 480 and the tines 36 and platform surface 34 of the subassembly 10 are passed beneath the posterior side surface 505 of the nucleus 500 which is then held by piercing and penetrating the surface 505 with the tines 36. As is depicted in FIG. 6, the cutting edge 24 of the penetrating or splitting member 20 is advanced by operator manipulation of the connected plunger 80 applying a force against and then penetrating the nucleus 500 as indicated in FIG. 7. The tines 36 immobilize the nucleus 500 from movement in the direction of movement of the member 20 in the plane of the figures. The member 20 is then withdrawn from the nucleus by operator withdrawal of the plunger. It should only be necessary to penetrate the nucleus once or a few times with the splitting member 20 to split the nucleus. It will be necessary to then repeat the process a number of times, attaching the tines to the larger fragments and breaking those fragments with the splitting member 20 in a similar fashion. As is diagrammatically depicted in FIG. 8, the resulting fragments 500' may be flushed through the limbal incision in a manner indicated by arrow 550 by the introduction of irrigation through the distal tip of the subassembly 110 of FIG. 3 or through another irrigating lumen 700 in a manner depicted by arrow 600. If desired, sufficiently small fragments can be aspirated by means of a partial vacuum applied to a lumen.

It is further envisioned that either of the elongated members 20 and 120 may be joined with the syringe plunger head in any of a number of ways including molding of the head about an end portion of the member, adhering the member to the head or providing complementary conventional mechanical mating structures (complementary screw threads, etc.) at the ends of the plunger head and member. Furthermore, although the device is described as utilizing a modification of a conventional syringe, other types of hand held mechanical arrangements are possible.

Having described specific embodiments of the present invention, it will be understood that further modifications and variations will be apparent and suggested to those skilled in the art and I intend to cover with my invention all subject modifications which fall within the scope of the appended claims.

I claim:

1. A nucleus splitter device comprising:
 (a) a hollow tubular body having a central axis;
 (b) an elongated member slidable within said tubular body along said axis, said elongated member including an end portion having a receiving means;
 (c) a platform structure extending from one end portion of the hollow tubular body;
 (d) a projecting member supported by said platform structure at an end of said platform remote from the tubular body and adapted for immobilizing a nucleus of a lens, in vivo,
  said projecting member having a plurality of projecting tines for piercing and holding said nucleus;
 (e) a solid, penetrating tip for splitting said nucleus, said penetrating tip being removably inserted in said receiving means of said elongated body, said penetrating tip including a progressively decreasing cross-section ending with a single piercing portion;

(f) a plunger means reciprocally mounted within said hollow tubular body, said plunger means including an end portion arranged to abut said elongated member to effect displacement thereof within said hollow tubular body whereby said penetrating tip is displaced in one direction only, to effect a controlled fragmentation of said nucleus.

2. The device of claim 1 wherein said hollow tubular body comprises a syringe body.

3. The device of claim 1 further comprising an irrigation means integral with said hollow body for supplying a fluid into a corneal incision during surgery, said irrigation means comprising a multiplicity of projections extending radially from and about an outer surface of said elongated member, said projections being arranged to center said elongated member in said tubular body to maintain a gap between said elongated member and an inner surface of said tubular body, said irrigation means having a hollow coupling projecting from a side of said tubular body for introducing said fluid into said hollow tubular body.

4. The device of claim 1, wherein said platform structure is curved and concave with respect to a center line of said penetrating tip.

5. The device of claim 1, wherein said tines are disposed at an acute angle with respect to said platform structure.

6. A method for removing a nucleus having a posterior and anterior chamber sides from an eye comprising:

(a) making a limbal incision in the eye;

(b) passing a nucleus splitting device having at least two tines through said incision and along at least part of the posterior chamber side of the nucleus;

(c) piercing said nucleus with said tines to immobilize said nucleus to prevent movement in at least a first direction;

(d) penetrating said immobilized nucleus not more than about three times with a solid penetrating member of said splitting device, said penetrating causing said nucleus to split in to a plurality of nucleus portions; and (e) irrigating said eye to flush out said nucleus portions, said irrigating step effecting the removal of said nucleus through said limbal incision.

* * * * *